US007833714B1

(12) United States Patent
Fodor

(10) Patent No.: US 7,833,714 B1
(45) Date of Patent: *Nov. 16, 2010

(54) COMBINATORIAL AFFINITY SELECTION

(75) Inventor: Stephen P. A. Fodor, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/566,888

(22) Filed: Dec. 5, 2006

Related U.S. Application Data

(62) Division of application No. 10/822,423, filed on Apr. 12, 2004, now abandoned.

(60) Provisional application No. 60/462,508, filed on Apr. 11, 2003.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3
(58) Field of Classification Search .................. None
See application file for complete search history.

(56) References Cited

U.S. PATENT DOCUMENTS

| 5,474,796 | A | * | 12/1995 | Brennan | 427/2.13 |
|---|---|---|---|---|---|
| 5,683,875 | A | | 11/1997 | Lichtenwalter | |
| 5,800,992 | A | | 9/1998 | Fodor et al. | |
| 6,300,063 | B1 | * | 10/2001 | Lipshutz et al. | 435/6 |
| 6,309,822 | B1 | | 10/2001 | Fodor et al. | |
| 6,551,784 | B2 | | 4/2003 | Fodor et al. | |
| 6,576,424 | B2 | | 6/2003 | Fodor et al. | |
| 2002/0048763 | A1 | * | 4/2002 | Penn et al. | 435/6 |

\* cited by examiner

*Primary Examiner*—Samuel Woolwine
(74) *Attorney, Agent, or Firm*—Thomas J. Siepmann

(57) ABSTRACT

In one aspect of the invention, methods for analyzing nucleic acid sample are provided. In a preferred embodiment, nucleic acids are selected using affinity matrices prior hybridization with a microarray.

13 Claims, 2 Drawing Sheets

US 7,833,714 B1

COMBINATORIAL AFFINITY SELECTION

REFERENCES TO RELATED APPLICATIONS

This application is a divisional application of and claims priority to U.S. patent application Ser. No. 10/822,423, filed Apr. 12, 2004, and claims priority to U.S. Provisional Patent Application Ser. No. 60/462,508, filed Apr. 11, 2003, each of which is incorporated herein by reference in its entirety.

FIELD OF THE INVENTION

The present invention relates to biological assays. More particularly, some embodiments of the invention are affinity selection.

BACKGROUND OF THE INVENTION

Nucleic acid affinity chromatography (see, e.g., U.S. Pat. No. 6,013,440, incorporated herein by reference) is based on the tendency of complementary, single-stranded nucleic acids to form a double-stranded or duplex structure through complementary base pairing. A nucleic acid (either DNA or RNA) can be attached to a solid substrate (matrix) where it acts as an immobilized ligand that interacts with and forms duplexes with complementary nucleic acids present in a solution contacted to the immobilized ligand. Unbound components can be washed away from the bound complex to either provide a solution lacking the target molecules bound to the affinity column, or to provide the isolated target molecules themselves. The nucleic acids captured in a hybrid duplex can be separated and released from the affinity matrix by denaturation either through heat, adjustment of salt concentration, or the use of a destabilizing agent such as formamide, TWEEN™-20 denaturing agent, or sodium dodecyl sulfate (SDS). Hybridization (the formation of duplex structure) between two nucleic acid sequences is highly sequence dependent. Sequences have the greatest affinity with each other where, for every purine in one sequence (nucleic acid) there exists a corresponding pyrimidine in the other nucleic acid and vice versa. This sequence dependency confers exquisite specificity on hybridization reactions and permits the preparation of affinity matrix that are highly selective for particular target nucleic acids. The target nucleic acids may be used for additional analysis.

SUMMARY OF THE INVENTION

In one aspect of the invention, methods are provided for nucleic acid analysis. In some embodiments, oligonucleotide affinity matrix is used for affinity capture of target nucleic acids. The captured target nucleic acids (on flat substrates, beads, etc.) are detected using spatially addressable oligonucleotides (such as microarrays, beads). In one embodiment, oligonucleotides are synthesized (or presynthesized and attached on) on beads. Each of the beads may contain at least 2, 4, 6, 10, 50, 100, 1000 different oligonucleotides. The oligonucleotides may be designed to hybridize with target nucleic acids to select specific sequences. A nucleic acid sample is hybridized with the beads. The beads may be washed to reduce nonspecific bindings. The captured nucleic acids (bound nucleic acids) may be eluted, for example, by more stringent hybridization conditions. The eluted nucleic acids may be hybridized to a microarray for detection.

The different oligonucleotides on beads may be synthesized by combinatorial synthesis.

In some embodiments, the oligonucleotides on the beads are designed to select (hybridize) nucleic acids representing certain transcripts (the transcripts themselves or nucleic acids derived from the transcript or their complementary sequences) or nucleic acids representing certain genotyping sites (DNA sequences containing the genotyping sites or nucleic acids derived from such DNA sequences or their complementary sequences). The selected nucleic acids may be hybridized with microarray chips that detects transcripts or genotyping microarray chips.

In one particularly preferred embodiment, oligonucleotides specific for splicing sites are immobilized (or synthesized on) on beads (each beads may contain different oligonucleotides). The oligonucleotides are used to select sequences representing splice sites. The selection can be used to reduce the complexity of the assay and data analysis. The oligonucleotides may be, for example, at least 30, 40, 50, 60 bases in length. Nucleic acid sample representing the splicing sites may be selected using the beads. The selected target nucleic acids may be hybridized with a microarray designed to interrogate the splicing sites to detect the forms of transcripts (forms of exon combination). The selection step may reduce cross hybridization.

In one embodiment, one set of beads are used to purify (select) one particular junction structure (e.g., exons 1, 2 or exons 2, 3 in a 3 exon gene). The purified nucleic acid from the first set is labeled with one color (e.g., fluorescent label) (C1). A second set is used to purify another set of junction structure (e.g., exons 1, 3 or 3, 4). The second set is labeled with a second color (C2). The resulting labeled nucleic acids are hybridized with a microarray that detects exons 1, 2, 3. The two color signals may be used to analyze relative abundance of alternatively splice transcripts. For example, the ratio C1/C2 may be indicative of relative abundance of different exon combinations.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

I. General

Figure 1:
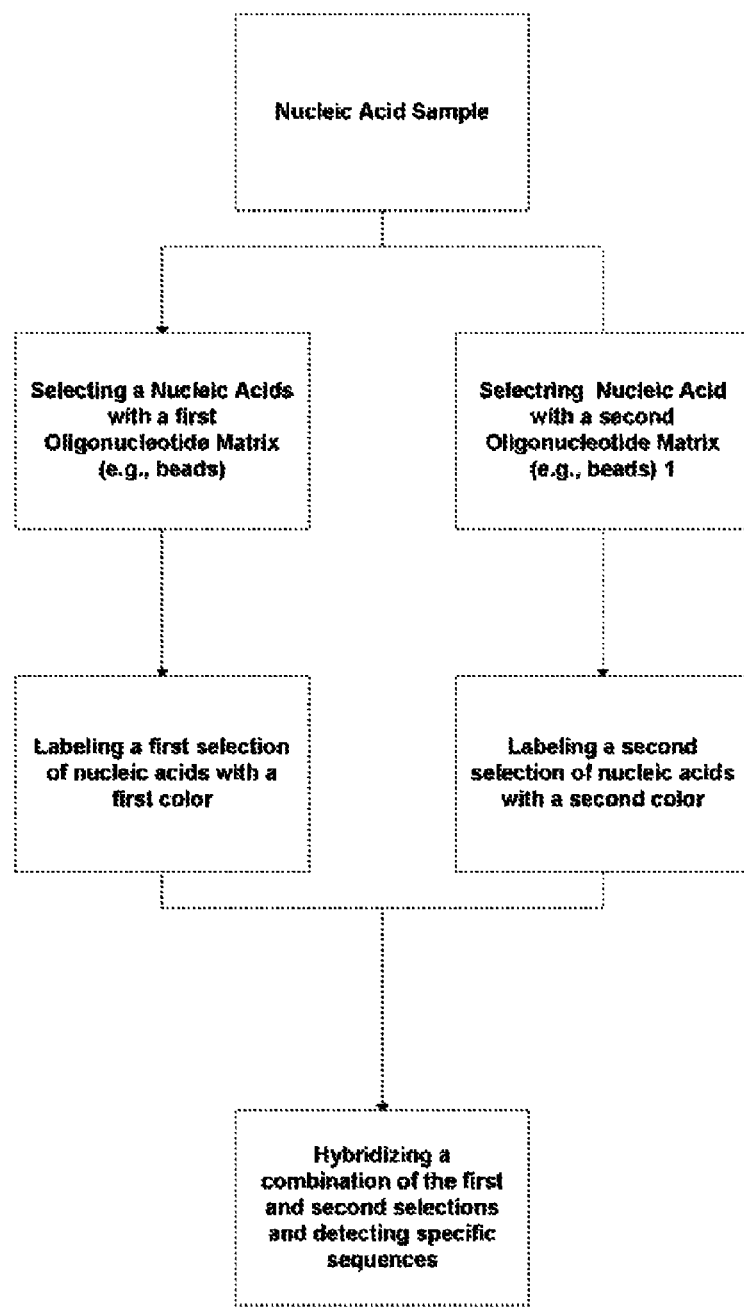
FIG. 1 is a schematic illustrating one exemplary embodiment of a method of the invention.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Stryer, L (1995) *Biochemistry* (4th Ed.) Freeman, New York, Gait, *"Oligonucleotide Synthesis: A Practical Approach"* 1984, IRL Press, London, Nelson and Cox (2000), Lehninger, *Principles of Biochemistry* 3$^{rd}$ Ed., W. H. Freeman Pub., New York, N.Y. and Berg et al. (2002) *Biochemistry,* 5$^{th}$ Ed., W. H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat Nos. 5,412,087, 6,147,205, 6,262,216, 6,310,189, 5,889,165, and 5,959,098.

Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. No. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,732, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17(1991); *PCR* (Eds. McPherson et al., IRL Press, Oxford); and U.S. Pat. Nos. 4,683,202, 4,683,195, 4,800,159, 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO 88/10315), self-sustained sequence replication (Guatelli et al., *Proc. Nat. Acad. Sci. USA,* 87, 1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. No. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y., 1989); Berger and Kimmel *Methods in Enzymology,* Vol. 152, *Guide to Molecular Cloning Techniques* (Academic Press, Inc., San Diego, Calif., 1987); Young and Davis, *P.N.A.S.* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U. S. patent application Ser. No. 60/364,731 and in PCT Application PCT/US99/06097 (published as WO 99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,732, 5,936,324, 5,981,956, 6,025,601, 6,090,555, 6,141,096, 6,185,030, 6,201,639, 6,218,803; and 6,225,625, In U.S. patent application Ser. No. 60/364,731 and in PCT Application PCT/US99/06097 (published as WO 99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology,* (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,785,716, 5,733,720, 5,974,164, 6,066,454, 6,090,555, 6,185,561, 6,188,783, 6,223,127, 6,229,911 and 6,308,170.

The present invention may also make use of the several embodiments of the array or arrays and the processing described in U.S. Pat. Nos. 5,545,531 and 5,874,219. These patents are incorporated herein by reference in their entireties for all purposes Additionally, the present invention may have preferred embodiments that include methods for providing genetic information over networks such as the Internet as shown in U.S. patent applications Ser. Nos. 10/063,559, 60/349,546, 60/376,003, 60/394,574, 60/403,381.

Definitions

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

Array Plate or a Plate a body having a plurality of arrays in which each array is separated from the other arrays by a physical barrier resistant to the passage of liquids and forming an area or space, referred to as a well.

Nucleic acid library or array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs) as described in U.S. Pat. No. 6,156,501 that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Biopolymer or biological polymer: is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DAN, and combinations of the above. "Biopolymer synthesis" is intended to encompass the synthetic production, both organic and inorganic, of a biopolymer.

Related to a bioploymer is a "biomonomer" which is intended to mean a single unit of biopolymer, or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers.

Initiation Biomonomer: or "initiator biomonomer" is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

Complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementary exist when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

Combinatorial Synthesis Strategy: A combinatorial synthesis strategy is an ordered strategy for parallel synthesis of diverse polymer sequences by sequential addition of reagents which may be represented by a reactant matrix and a switch matrix, the product of which is a product matrix. A reactant matrix is a l column by m row matrix of the building blocks to be added. The switch matrix is all or a subset of the binary numbers, preferably ordered, between 1 and m arranged in columns. A "binary strategy" is one in which at least two successive steps illuminate a portion, often half, or a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

Effective amount refers to an amount sufficient to induce a desired result.

Excitation energy refers to energy used to energize a detectable label for detection, for example illuminating a fluorescent label. Devices for this use include coherent light or non coherent light, such as lasers, UV light, light emitting diodes, an incandescent light source, or any other light or other electromagnetic source of energy having a wavelength in the excitation band of an excitable label, or capable of providing detectable transmitted, reflective, or diffused radiation.

Genome is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

Hybridization conditions will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Hybridizations, e.g., allele-specific probe hybridizations, are generally performed under stringent conditions. For example, conditions where the salt concentration is no more than about 1 Molar (M) and a temperature of at least 25° C., e.g., 750 mM NaCl, 50 mM NaPhosphate, 5 mM EDTA, pH 7.4 (5× SSPE) and a temperature of from about 25° C. to about 30° C.

Hybridizations are usually performed under stringent conditions, for example, at a salt concentration of no more than 1 M and a temperature of at least 25° C. For example, conditions of 5× SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning: A laboratory Manual" $2^{nd}$ Ed. Cold Spring Harbor Press (1989) which is hereby incorporated by reference in its entirety for all purposes above.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

Hybridization probes are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics. See U.S. Pat. No. 6,156,501.

Hybridizing specifically to: refers to the binding, duplexing, or hybridizing of a molecule substantially to or only to a particular nucleotide sequence or sequences under stringent conditions when that sequence is present in a complex mixture (e.g., total cellular) DNA or RNA.

Isolated nucleic acid is an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

Label for example, a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). See U.S. Pat. No. 6,287,778.

Ligand: A ligand is a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies.

Linkage disequilibrium or allelic association means the preferential association of a particular allele or genetic marker with a specific allele, or genetic marker at a nearby chromosomal location more frequently than expected by chance for any particular allele frequency in the population.

For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

Microtiter plates are arrays of discrete wells that come in standard formats (96, 384 and 1536 wells) which are used for examination of the physical, chemical or biological characteristics of a quantity of samples in parallel.

Mixed population or complex population: refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

Monomer: refers to any member of the set of molecules that can be joined together to form an oligomer or polymer. The set of monomers useful in the present invention includes, but is not restricted to, for the example of (poly)peptide synthesis, the set L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

mRNA or mRNA transcripts: as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein; a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

Nucleic acid library or array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Nucleic acids according to the present invention may include any polymer or oligomer of pyrimidine and purine bases, preferably cytosine, thymine, and uracil, and adenine and guanine, respectively. See Albert L. Lehninger, Principles of Biochemistry, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

Probe: A probe is a surface-immobilized molecule that can be recognized by a particular target. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Primer is a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 20, 25, 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

Reader or plate reader is a device which is used to identify hybridization events on an array, such as the hybridization between a nucleic acid probe on the array and a fluorescently labeled target. Readers are known in the art and are commercially available through Affymetrix, Santa Clara Calif. and other companies. Generally, they involve the use of an excitation energy (such as a laser) to illuminate a fluorescently labeled target nucleic acid that has hybridized to the probe. Then, the reemitted radiation (at a different wavelength than the excitation energy) is detected using devices such as a CCD, PMT, photodiode, or similar devices to register the collected emissions. See U.S. Pat. No. 6,225,625.

Receptor: A molecule that has a affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

Target: A molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides,nucleic acids, peptides, cofactors, lectins, sugars. polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

WGSA (Whole Genome Sampling Assay) Genotyping Technology: A technology that allows the genotyping of thousands of SNPs simultaneously in complex DNA without the use of locus-specific primers. In this technique, genomic DNA, for example, is digested with a restriction enzyme of interest and adaptors are ligated to the digested fragments. A single primer corresponding to the adaptor sequence is used to amplify fragments of a desired size, for example, 500-2000 bp. The processed target is then hybridized to nucleic acid arrays comprising SNP-containing fragments/probes. WGSA is disclosed in, for example, U.S. Provisional Application Ser. Nos. 60/319,685, 60/453,930, 60/454,090 and 60/456,206, 60/470,475, U.S. patent application Ser. Nos. 09/766,212, 10/316,517, 10/316,529, 10/463,991, 10/321, 741, 10/442,021 and 10/254,945, each of which is hereby incorporated by reference in its entirety for all purposes.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

II. Combinatorial Affinity Selection

In one aspect of the invention, methods are provided for complexity reduction for nucleic acid analysis. In some embodiments, a nucleic acid sample is hybridized with one or more nucleic acid affinity matrices to select sets of nucleic acids for additional analysis.

The term nucleic acid "affinity matrix", as used herein, refers to a solid support or gel to which is attached a multiplicity of different oligonucleotides. The Nucleic acid affinity matrix and methods of manufacturing were described in, e.g., U.S. Pat. No. 6,013,440, which is incorporated by reference for all purposes. The solid support with internal or external surface may be in any suitable format including beads, flat substrate, tubes, tunnels, channels, etc. The support can be porous, which may provide internal surface for the immobilization of oligonucleotides and for hybridization to occur. Preferred matrix materials do not interfere with subsequent hybridization of attached oligonucleotides. Suitable matrix materials include, but are not limited to paper, glasses, ceramics, metals, metalloids, polacryloylmorpholide, various plastics and plastic copolymers such as Nylon.TM., Teflon.TM., polyethylene, polypropylene, poly(4-methylbutene), polystyrene, polystyrene, polystyrene/latex, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and controlled-pore glass (Controlled Pore Glass, Inc., Fairfield, N.J.), aerogels (see, e.g., Ruben et al., J. Materials Science 27, 4341-4349 (1992); Rao et al., J. Material Science 28, 3021 (1993); Back et al., J. Phys. D. appl. Phys. 22, 7309-734 (1989); Kim & Jang, J. Am. Ceram. Soc. 74, 1987-92 (1991) and the like, and other materials generally known to be suitable for use in affinity columns (e.g. HPLC columns).

The affinity matrices may also include beads (or other small objects which provide suitable surfaces) that are identifiable individually or in groups. For example, the beads may be coded with oligonucleotides. The affinity matrices may also be separable according their magnetic properties.

Hybridization of the nucleic acid sample to the affinity matrix will result in duplex formation between the affinity ligands and their target nucleic acids. Upon elution of the sample from the affinity matrix, the matrix will retain the duplexes nucleic acids leaving a sample depleted of the overexpressed target nucleic acids.

The affinity matrix can also be used to identify unknown mRNAs or cDNAs in a sample. Where the affinity matrix contains nucleic acids complementary to every known gene (e.g., in a cDNA library, DNA reverse transcribed from an mRNA, mRNA used directly or amplified, or polymerized from a DNA template) in a sample, capture of the known nucleic acids by the affinity matrix leaves a sample enriched for those nucleic acid sequences that are unknown. In effect, the affinity matrix is used to perform a subtractive hybridization to isolate unknown nucleic acid sequences. The remaining "unknown" sequences can then be purified and sequenced according to standard methods.

The affinity matrix can also be used to capture (isolate) and thereby purify unknown nucleic acid sequences. For example, an affinity matrix can be prepared that contains nucleic acid (affinity ligands) that are complementary to sequences not previously identified, or not previously known to be expressed in a particular nucleic acid sample. The sample is then hybridized to the affinity matrix and those sequences that are retained on the affinity matrix are "unknown" nucleic acids. The retained nucleic acids can be eluted from the matrix (e.g. at increased temperature, increased destabilizing agent concentration, or decreased salt) and the nucleic acids can then be sequenced according to standard methods.

Similarly, the affinity matrix can be used to efficiently capture (isolate) a number of known nucleic acid sequences. Again, the matrix is prepared bearing nucleic acids complementary to those nucleic acids it is desired to isolate. The sample is contacted to the matrix under conditions where the complementary nucleic acid sequences hybridize to the affinity ligands in the matrix. The non-hybridized material is washed off the matrix leaving the desired sequences bound. the hybrid duplexes are then denatured providing a pool of the isolated nucleic acids. The different nucleic acids in the pool can be subsequently separated according to standard methods (e.g. gel electrophoresis).

Ad indicated above the affinity matrices can be used to selectively remove nucleic acids from virtually any sample containing nucleic acids (e.g., in a cDNA library, DNA reverse transcribed from an mRNA, mRNA used directly or amplified, or polymerized from a DNA template, and so forth). The nucleic acids adhering to the column can be removed by washing with a low salt concentration buffer, a buffer containing a destabilizing agent such as formamide, or by elevating the column temperature.

In one particularly preferred embodiment, the affinity matrix can be used in a method to enrich a sample for unknown RNA sequences (e.g. expressed sequence tags (ESTs)). The method involves first providing an affinity matrix bearing a library of oligonucleotide probes specific to known RNA (e.g., EST) sequences Then, RNA from undifferentiated and/or unactivated cells and RNA from differentiated or activated or pathological (e.g., transformed) or otherwise having a different metabolic state are separately hybridized against the affinity matrices to provide two pools of RNAs lacking the known RNA sequences.

The RNAs from the differentiated (or activated, etc.) cells are reverse, transcribed to produce cDNAs bearing cleavable PCR priming regions. (See, e.g., Van Gelder, et al., Proc. Natl Acad. Sci. USA, 87:1663-1667 (1990) and Eberwine et al. Proc. Natl. Acad. Sci. USA, 89:3010-3014). Similarly, the RNAs from the undifferentiated cells are reverse transcribed to make cDNAs without PCR priming sites. The two resulting pools of cDNAs are then combined with the cDNAs from the undifferentiated cells in great excess (e.g. at least 10 fold excess). At this high concentration, during PCR the cDNAs from the undifferentiated cells will hybridize with complementary sequences from the differentiated cells and form stable duplexes thereby preventing amplification of the corresponding sequences. Conversely, those nucleic acids unique to the differentiated cells are differentially amplified. Thus, the PCR effectively performs a subtractive hybridization resulting in a nucleic acid sample enriched for unknown ESTs that are characteristic of the activated or differentiated state. In one aspect of the invention, methods are provided for nucleic acid analysis. In some embodiments, oligonucleotide affinity matrix is used for affinity capture of target nucleic acids. The captured target nucleic acids (on flat substrates, beads, etc.) are detected using spatially addressable oligonucleotides (such as microarrays, beads). In one embodiment, oligonucleotides are synthesized (or presynthesized and attached on) on beads. Each of the beads may contain at least 2, 4, 6, 10, 50, 100, 1000 different oligonucleotides. The oligonucleotides may be designed to hybridize with target nucleic acids to select specific sequences. A nucleic acid sample is hybridized with the beads. The beads may be washed to reduce nonspecific bindings. The captured nucleic acids (bound nucleic acids) may be eluted, for example, by more stringent hybridization conditions. The eluted nucleic acids may be hybridized to a microarray for detection.

The different oligonucleotides on beads may be synthesized by combinatorial synthesis.

In some embodiments, the oligonucleotides on the beads are designed to select (hybridize) nucleic acids representing certain transcripts (the transcripts themselves or nucleic acids derived from the transcript or their complementary sequences) or nucleic acids representing certain genotyping sites (DNA sequences containing the genotyping sites or nucleic acids derived from such DNA sequences or their complementary sequences). The selected nucleic acids may be hybridized with microarray chips that detects transcripts or genotyping microarray chips.

In one particularly preferred embodiment, oligonucleotides specific for splicing sites are immobilized (or synthesized on) on beads (each beads may contain different oligonucleotides). The oligonucleotides are used to select sequences representing splice sites. The selection can be used to reduce the complexity of the assay and data analysis. The oligonucleotides may be, for example, at least 30, 40, 50, 60 bases in length. Nucleic acid sample representing target transcripts may be hybridized with the beads. The target nucleic acids representing the splicing sites may be selected using the beads. The selected target nucleic acids may be hybridized with a microarray designed to interrogate the splicing sites to detect the forms of transcripts (forms of exon combination). The selection step may reduce cross hybridization.

In one embodiment, one set of beads are used to purify (select) one particulary junction structure (e.g., exons 1, 2 or exons 2, 3 in a 3 exon gene). The purified nucleic acid from the first set is labeled with one color (e.g., fluorescent label) (C1). A second set is used to purify another set of junction structure (e.g., exons 1, 3 or 3, 4). The second set is labeled with a second color (C2). The resulting labeled nucleic acids are hybridized with a microarray that detects exons 1, 2, 3. The two color signals may be used to analyze relative abundance of alternatively splice transcripts. For example, the ratio C1/C2 may be indicative of relative abundance of different exon combinations.

In a preferred embodiment (illustrated in FIG. 1), the method includes selecting a first and second sets of nucleic acids from the nucleic acid sample with a first and second nucleic acid affinity matrices, where the first and second nucleic acid affinity matrices hybridizes with two different set of nucleic acids; labeling the first and second sets of nucleic acids with different labels; and detecting the first and second sets of nucleic acids based upon the different labels. In some embodiments, there may be more than 2, 3, 4, 5, 10, 50, 100 different affinity matrices, which can result in many different nucleic acid sets.

Typically, the affinity matrices have oligonucleotides that hybridizes with a different sets of nucleic acids. The different sets may be labeled with different markers such as fluorescent labels with different excitation or emission spectrums ("colors").

The different sets may be mixed and then hybridize with a microarray or sequentially hybridized with a microarray for detection. Microarray analysis technology is well known in the art and are described in numerous references previously incorporated by reference.

Figure 2:
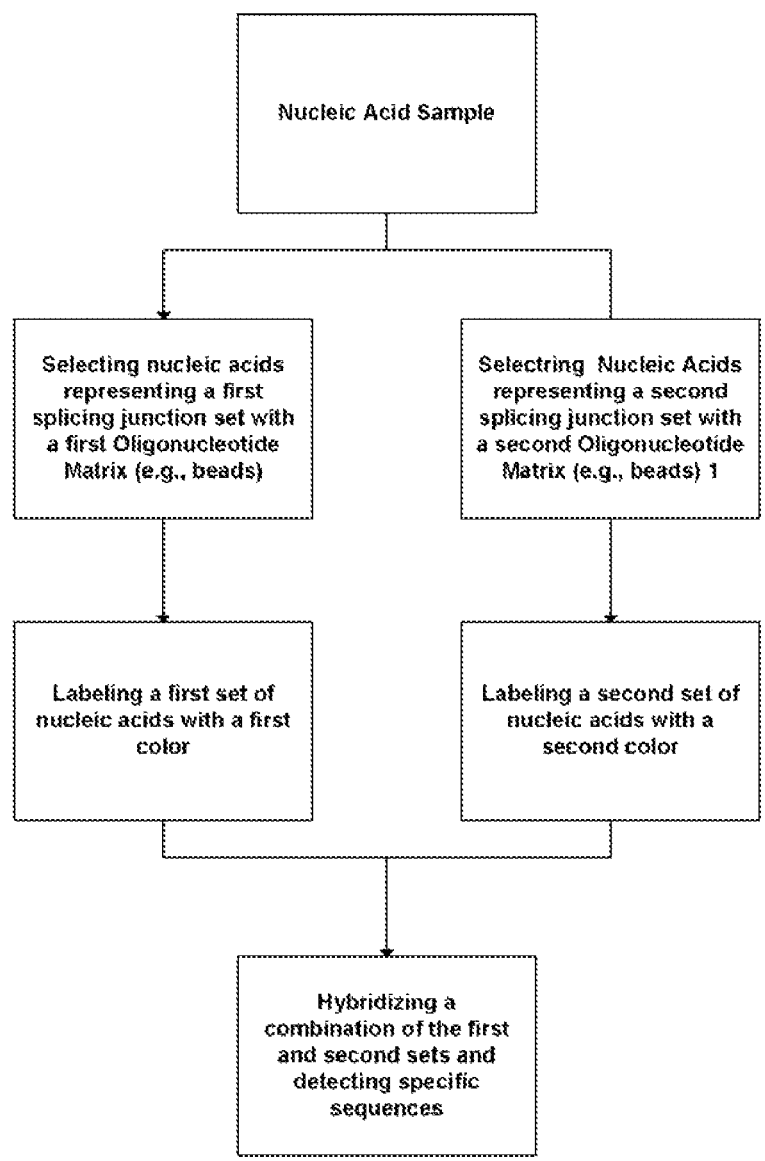
FIG. 2 is a schematic illustrating one exemplary embodiment of a method for detecting alternative splicing.

The selection and analysis protocol are useful for reducing the complexity of a nucleic acid sample to be analyzed. In one preferred embodiment, this method is used to reduce the complexity of a genomic sample for genotyping analysis. In another preferred embodiment, the method is used for analyzing alternative splicing (FIG. 2). In one exemplary method, a nucleic acid sample representing transcripts (typically, a nucleic acid sample that contains the transcripts or nucleic acids derived from the transcripts via template driven nucleic acids reactions, such as PCR, reverse transcription, transcription, etc.). In one embodiment, the nucleic acid sets are analyzed separately. In another embodiment (FIG. 2), the nucleic acids are selectively labeled with different labels based upon their hybridization of affinity matrices. For example, collection of nucleic acid representing splice junctions may be selected and labeled with different labels to facilitate the detection with microarrays for such junctions.

As one of skill in the art would appreciate, this method can also be used to facilitate the detection of exon and intron sequences.

In one particularly preferred embodiment, affinity matrix against one particular exon may be used to select nucleic acids represent the transcripts with this particular exon. The selected nucleic acids then can be analyzed, e.g., using a microarray, for the exons that are present with the particular exon.

CONCLUSION

It is to be understood that the above description is intended to be illustrative and not restrictive. Many variations of the invention will be apparent to those of skill in the art upon reviewing the above description. All cited references, including patent and non-patent literature, are incorporated herein by reference in their entireties for all purposes.

What is claimed is:

1. A method for detecting and quantitating relative ratios of different nucleic acid sequence variants comprising:
    selecting a first set of nucleic acids comprising a first target nucleic acid sequence from a sample comprising a mixture of nucleic acid sequences with a first nucleic acid affinity matrix comprising nucleic acid probes bound to at least one bead, said probes synthesized by combinatorial synthesis, wherein the first nucleic acid affinity matrix hybridizes, under stringent conditions comprising a salt concentration of 1 M and a temperature of at least 25° C., with the first set of nucleic acids;
    selecting a second set of nucleic acids comprising a second target nucleic acid sequence from the sample with a second nucleic acid affinity matrix comprising nucleic acid probes bound to at least one bead, said probes synthesized by combinatorial synthesis, wherein the second nucleic acid affinity matrix hybridizes, under stringent conditions comprising a salt concentration of 1 M and a temperature of at least 25° C., with the second set of nucleic acids;
    binding the sample with the affinity matrices;
    washing the affinity matrices;
    eluting the selected nucleic acids that are bound to the affinity matrices;
    labeling the first set of selected nucleic acids with a first label;
    labeling the second set of selected nucleic acids with a second label, wherein the second label is not the same as the first label;
    hybridizing the first set of selected nucleic acids and the second set of selected nucleic acids to an array comprising probes which hybridize to the first and the second set of selected nucleic acids; and
    detecting the first and second labels bound to the array, thereby quantitating the relative amounts of the first and second sets of selected nucleic acids.

2. The method according to claim 1, wherein the first label is a first color and the second label is a second color, and wherein the first color and the second color are not the same.

3. The method according to claim 1, wherein the labels are fluorescent labels.

4. The method according to claim 1, wherein the first set of selected nucleic acids and the second set of nucleic acids are mixed together prior to hybridization to the array.

5. The method according to claim 1, wherein the sample comprises transcript sequences.

6. The method according to claim 5, wherein the first nucleic acid affinity matrix comprises probes complementary to a first transcript splice variant, wherein the second nucleic acid affinity matrix comprises probes complementary to a second transcript splice variant, and wherein the first and second transcript variants comprise different splice variant sequences.

7. The method according to claim 1, wherein the first nucleic acid affinity matrix comprises probes complementary to a first sequence genotype, and wherein the second nucleic acid affinity matrix comprises probes complementary to a second sequence genotype whose sequence differs from the first sequence genotype by a single nucleotide polymorphism.

8. The method according to claim 1, further comprising additional affinity matrices and corresponding different labels, allowing selection and relative quantitation of more than two different nucleic acid sequences.

9. The method according to claim 1, wherein the beads are identified with coded oligonucleotides.

10. The method according to claim 1, further comprising separation of the affinity matrices according to their magnetic properties.

11. The method according to claim 1, wherein the beads comprise at least 100 different oligonucleotides.

12. The method according to claim 1, wherein the beads comprise at least 1000 different oligonucleotides.

13. The method according to claim 1, wherein the probes are synthesized on the beads.

* * * * *